US009713544B2

(12) United States Patent
Barbosa

(10) Patent No.: US 9,713,544 B2
(45) Date of Patent: Jul. 25, 2017

(54) POSTURE CORRECTION REMINDER

(71) Applicant: Vera L. Barbosa, El Paso, TX (US)

(72) Inventor: Vera L. Barbosa, El Paso, TX (US)

( * ) Notice: Subject to any disclaimer, the term of this patent is extended or adjusted under 35 U.S.C. 154(b) by 1112 days.

(21) Appl. No.: 13/891,987

(22) Filed: May 10, 2013

(65) Prior Publication Data

US 2014/0336555 A1    Nov. 13, 2014

(51) Int. Cl.
*A61F 5/02* (2006.01)

(52) U.S. Cl.
CPC .................... *A61F 5/026* (2013.01)

(58) Field of Classification Search
CPC ...... A61F 5/00; A61F 5/01; A61F 5/02; A61F 5/028; A61F 5/026; A61F 5/024; A61F 5/30; A61F 5/37; A61H 2201/00; A61H 2201/16; A61H 2201/1602; A61H 2201/1614; A61H 2201/1616; A61H 2201/165; A61H 2201/1652; A41F 15/00; A41F 15/002; A41F 15/007; A41F 15/02; A41F 3/02
USPC .......... 602/5, 12, 19, 20; 128/846, 869, 870, 128/873, 875, 876
See application file for complete search history.

(56) References Cited

U.S. PATENT DOCUMENTS

| | | | |
|---|---|---|---|
| 1,050,257 A | 1/1913 | Trigg | |
| 1,715,196 A * | 5/1929 | Glass | A61F 5/026 2/327 |
| 2,463,194 A | 3/1949 | Meyer | |
| 5,135,470 A | 8/1992 | Reeves | |
| 5,466,214 A | 11/1995 | Calderon-Garciduenas | |
| 5,816,251 A | 10/1998 | Glisan | |
| 6,336,908 B1 | 1/2002 | Slautterback | |
| 6,766,532 B1 | 7/2004 | Cabana | |
| 7,322,952 B2 | 1/2008 | Chase et al. | |
| 2003/0195445 A1 | 10/2003 | Behan | |
| 2008/0319364 A1 | 12/2008 | Josey | |

FOREIGN PATENT DOCUMENTS

DE        202009008660        9/2009

OTHER PUBLICATIONS

International Search Report and Written Opinion issued in corresponding PCT Patent App. No. PCT/US14/33312 dated Sep. 16, 2014 (9 pages).

* cited by examiner

*Primary Examiner* — Kari Rodriquez
(74) *Attorney, Agent, or Firm* — Dykema Gossett P.L.L.C.

(57) ABSTRACT

A wearable apparatus is configured to be worn by an individual and includes left and right shoulder loops which are connected through intermediate strap segments to at least one connector. The wearable apparatus further includes at least one bottom strap connected to the at least one connector and configured with a fastener that may be used to reversibly mount the bottom strap to the beltline of the wearer. The apparatus is configured such that if the wearer slouches forward the apparatus provides a force reminding the individual to maintain proper posture.

5 Claims, 11 Drawing Sheets

POSTURE CORRECTION REMINDER

FIELD

The disclosed subject matter relates to an apparatus for encouraging a person to maintain proper posture.

BACKGROUND

Maintaining proper posture is an important aspect of overall health. Poor posture may contribute to the development of various health conditions including lower back pain, the presence of headaches, and chronic pain in the shoulders. Moreover, individuals who typically have poor posture, which may be manifested as an imbalance of stress and excess strain in the spine, back, and neck, may generally be more susceptible to stress-induced injuries than other individuals who do maintain proper posture. Problems associated with or caused by poor posture may be a particular concern for some members of the population, such as the elderly and individuals with sedentary lifestyles, who may be particularly susceptible to loss of muscle tone. Importantly, loss of muscle tone may be either or both of a cause and a symptom of poor posture, and if poor posture is uncorrected, some individuals may be subject to a debilitating cycle of chronic injury, pain, and a loss of mobility leading to a further decline in health. In addition, the benefits of maintaining proper posture extend to individuals with a wide range of fitness levels including those with generally good health. For example, individuals participating in athletics may recover from workouts more rapidly if they avoid slouching forward, and those individuals may generally be less prone to injury.

An individual's posture also serves as an important non-verbal cue associated with the individual's emotional state. When one stands tall, they project confidence and are typically viewed in a more attractive, authoritative, and overall positive light by others. In addition, posture not only influences how others perceive an individual, but also may influence how a person views his or herself. Individuals with good posture will generally feel more confident about themselves, and they are more likely to project this image to the outside world.

For some individuals, an apparatus that actively supports the spine in a proper alignment may be desirable. However, for some individuals, it may be desirable to encourage the individual to use their own musculature to support their spine, and to do so without assistance from external support material. When musculature is tasked with supporting proper alignment, loss of muscle tone may be minimized, and in some cases, prompting an individual to use their own musculature in order to maintain correct posture may, at least in part, reverse the effects of years of improper posture. Thus, for any of various reasons, there is a need for a wearable apparatus that encourages an individual to maintain correct posture.

SUMMARY

An apparatus for encouraging a wearer to maintain proper posture including a connector positioned along the axis of the spine of the wearer and at a vertical position between the shoulder blades and the waistline of the wearer when the apparatus is worn, a right strap including a loop portion and an intermediate segment, wherein the intermediate segment of the right strap extends from the loop portion of the right strap to said connector; a left strap including a loop portion and an intermediate segment, wherein the intermediate segment of the left strap extends from the loop portion of the left strap to the connector; a bottom strap connected to the connector at a first end; and a fastener connected to the bottom strap at one end and at another end configured for attachment to an article of clothing near the beltline of the wearer; wherein the loop portions of the right strap and the left strap are each configured for adjustment in size, and configured to securely fashion around the shoulders of the wearer; wherein the apparatus is configured such that if the wearer slouches forward a force sufficient to remind the user to adopt proper posture is applied to the shoulders of said wearer.

DETAILED DESCRIPTION

Figure 1:
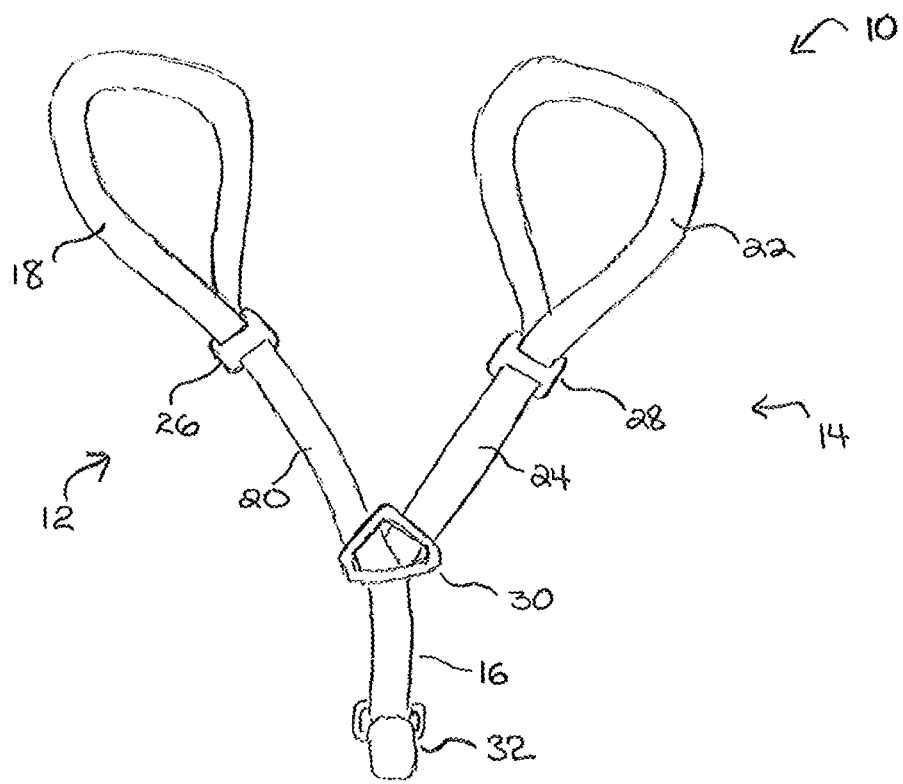
FIG. 1 is a front perspective view of an embodiment of an apparatus for reminding a wearer to maintain proper posture.

The following terms as used herein should be understood to have the indicated meanings When an item is introduced by "a" or "an," it should be understood to mean one or more of that item.

"Comprises" means includes but is not limited to.

"Comprising" means including but not limited to.

"Having" means including but not limited to.

The term "fabric" means a material made by weaving, knitting, felting, or other suitable processing of a cloth material, such as, by way of nonlimiting example, wool, hair, silk, flax, cotton, or any combinations thereof.

The term "chape" means a part of a connector that may be fixed or secured in place on a strap. A chape may be used to fix the position of a connector, such as a buckle, in place and still enable a second end of a connector to engage with another strap portion or strap end.

This disclosure is generally directed to a wearable apparatus that is designed to encourage or remind an individual to maintain proper posture. Particularly, the shoulders of a person should be maintained in proper posture, namely a position sufficiently backwards with respect to the spine, in order to encourage the spine to adopt a natural S-shape thereby providing a balanced distribution of forces on the vertebrae. When an individual has poor posture, the shoulders of an individual typically move forward, the natural curvature of the spine may be distorted and pressure on ligaments and spinal vertebrae may increase. If uncorrected, the poor posture may lead to a number of health-related problems. Ideally, an individual would be driven to maintain proper posture using their own musculature. Using one's own muscles to maintain proper posture helps keep important muscles of the back, neck, and shoulders strong thereby avoiding muscle atrophy that may be either or both of a cause and a symptom of chronic poor posture. For an individual wearing an apparatus as described herein, if the wearer slouches forward, straps of the apparatus are placed in tension, and the apparatus may apply a gentle force to the shoulders sufficient to remind the wearer that their posture is not proper. However, when a wearer maintains correct posture, the apparatus may not apply a significant force to the shoulders, is comfortable to wear, and does not help support an individual's spine.

Posture reminder apparatuses described herein may be worn by a user in a number of different ways. For example, a posture reminder apparatus may be worn on top of or underneath clothing, and it may be configured to rest upon an undershirt or bra. In some embodiments, a posture reminder apparatus may be suitably constructed such that it may be comfortably worn with shoulder loop straps or other components in direct contact with a user's skin. In some embodiments, a portion of a reminder apparatus in contact with the skin may include a pad configured to facilitate comfort. For example, a portion of a reminder apparatus, such as a pad or other element, may be suitably shaped, made from a suitable material, laminated, processed in some other way, or configured using any combination of techniques thereof to encourage comfort. A pad or other portion of a reminder apparatus that rests or which may come in contact with the skin of a wearer may be configured to slide across skin of a wearer without chaffing the skin or may be configured to prevent sliding.

Posture reminder apparatuses described herein may, in some embodiments, be combined directly with a unit of clothing. For example, a posture reminding apparatus may be attached, such as by weaving or using other means, directly to a unit of clothing. By way of nonlimiting example, a posture reminding apparatus may be combined with a shirt, blouse, undergarment, dress, or other article of clothing.

In some embodiments, an apparatus for reminding a wearer to correct their posture may be integrated in an article of clothing such as a shirt, dress, undershirt, undergarment, or bra, but the clothing may be made from lightweight flexible material that may not assist the individual to maintain proper posture. In some embodiments, an apparatus for reminding a wearer of their posture may be integrated in an article of clothing but only loosely connected to the article of clothing or otherwise bonded in such a way that the article of clothing may not assist the individual to maintain their posture. For example, in some embodiments, an article of clothing may be stitched or connected to a posture reminding apparatus intermittently and even if straps of the apparatus are placed under tension, such as when a wearer slouches forward, clothing may freely flow and may not be stretched.

In some embodiments, an article of clothing may comprise a fabric suitably shaped, for example, and without limitation, as a shirt, dress, undershirt, undergarment, or bra and further include a posture reminder apparatus comprising or consisting of straps, connectors, and fasteners as further illustrated in the embodiments herein.

Figure 2:
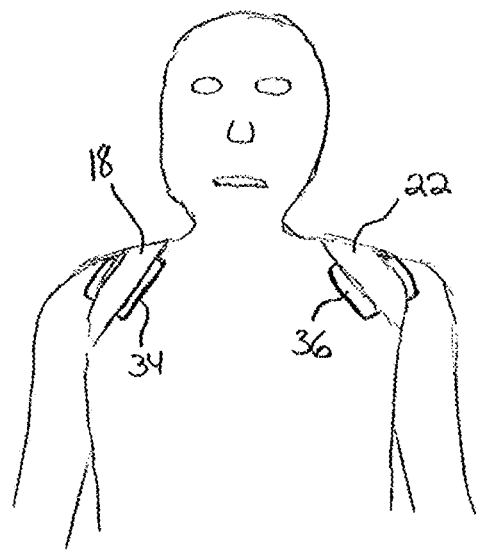
FIG. 2 shows an embodiment of an apparatus for reminding a wearer to maintain proper posture worn by an individual as viewed from the front.
Figure 3:
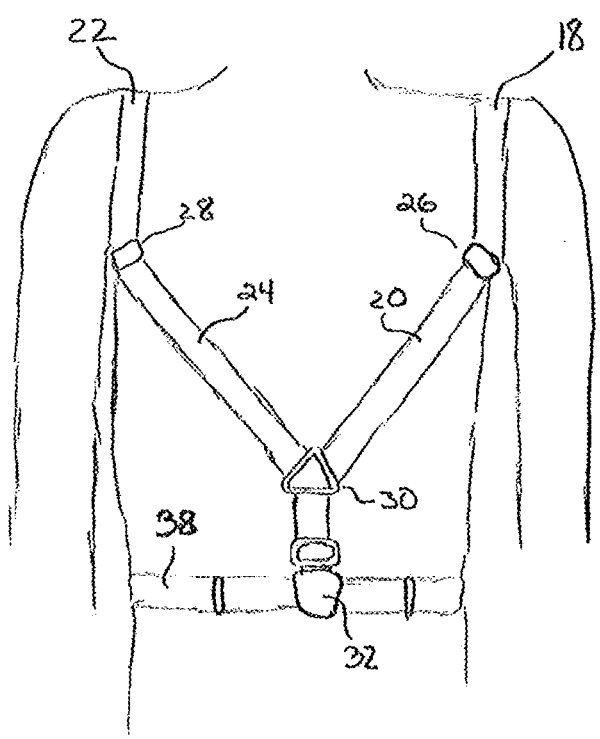
FIG. 3 shows an embodiment of an apparatus for reminding a wearer to maintain proper posture worn by an individual as viewed from the back.

FIG. 1 shows an apparatus 10 useful for applying a force sufficient to remind an individual to maintain proper posture if, for example, the individual slouches forward. In FIG. 2, apparatus 10 is shown worn by an individual as viewed from the front. In FIG. 3, apparatus 10 is shown worn by an individual as viewed from the back. Referring to FIGS. 1-3, posture reminder apparatus 10 may have a right strap 12, a left strap 14, and a bottom strap 16. Right strap 12 may include a right shoulder loop portion 18 and a right intermediate segment 20. Similarly, left strap 14 may include a left shoulder loop portion 22 and a left intermediate segment 24. A connector 26, 28 may divide a shoulder loop portion 18, 22 and intermediate segment 20, 24 of a given strap 12, 14. For example, as shown in FIG. 1, connector 26 may be a buckle configured to hold right shoulder loop portion 18 in place when engaged by an end of the right strap 12. Likewise, connector 28 may be a buckle configured to hold left shoulder loop portion 22 in place when engaged by an end of the left strap 14. An individual may adjust the size of a desired loop portion by adjusting the engagement of an associated buckle and strap end. Posture reminder apparatus 10 may also include an additional connector 30 positioned at the union of the right strap 12, the left strap 14, and the bottom strap 16. Bottom strap 16 may extend from connector 30 to a fastener 32.

As shown in FIGS. 2 and 3, shoulder loop portions 18, 22 of straps 12, 14 may be sized to fit comfortably around shoulders of an individual wearing posture correction apparatus 10. As shown in FIG. 2, apparatus 10 may, in some embodiments, include a pad or padded section 34, 36 which may be fashioned from an appropriate material in order to be comfortably worn and not chafe the skin of a wearer. A pad or padded section 34, 36 may be fixedly connected to a strap or may be removably associated with a given strap. For example, a pad may be mountable upon a strap using buttons or other suitable elements configured for reversibly connecting the pad. A pad or padded section of a reminder apparatus may be mounted or connected at a region where a reminder apparatus may rest or otherwise in motion tend to come in contact with a wearer's skin. In some embodiments, a pad or padded section may also be associated with one or more connectors of an apparatus. For example, in some embodiments, a pad or padded section may be configured for placement on the side of connector 30 that faces the skin of a wearer. As shown in FIG. 3, a posture reminder apparatus 10 may be reversibly attached to a belt 38 using a fastener 32 which may be a clip.

The straps 12, 14, and 16 may be made from a single piece of material or from two or more pieces of material fixedly or reversibly connected together. For example, different pieces of a strap may be fixedly connected using bonding or stitching techniques or joined together using other methods. In addition, by way of nonlimiting example, straps or portions of a strap may be connected using connectors, Velcro™, hook and loop fasteners, rings, clasps, clips, fasteners, snap fasteners, other suitable elements, or combinations thereof. A strap 12, 14 or part of a strap may be made from one or more materials that are suitably elastic such that a wearer may engage in normal movements without discomfort. However, a strap or part of a strap may be of sufficient strength and resilience such that it remains secure on the shoulders of a wearer. A strap or strap portion may be made from any of various materials, such as one or more fabrics, natural or synthetic polymers, rubbers, elastomers, other suitable materials or combinations thereof. In some embodiments, a strap or strap portion may be made from neoprene. A strap may be sized and shaped in various ways. A strap may, for example, be conveniently shaped with a rectangular cross section but may also be a thin circularly shaped element. In some embodiments, a strap element or elements may be shaped or sized such that they may be concealed when integrated with a unit of clothing or shaped as appropriate to be integrated in a decorative manner with an article of clothing.

The physical characteristics of a strap or portion of a strap may, in some embodiments, be adjusted by selecting an appropriate material and processing the material, such as by lamination of either or both sides of the material, stitching, quilting, other treatment methods, or combinations of the aforementioned methods. In some embodiments, a portion of a strap may be treated to adjust the relative strength and elasticity of a material, and it may, in some embodiments, be desirable to do so. For example, it may be desirable to make a strap 12, 14, 16 or combination of straps from a single piece of material, but desirable for a shoulder loop portion 18, 22 of a strap 12, 14 to exhibit greater stiffness than that of an intermediate segment 20, 24. If shoulder loop portions 18, 22 are modified to increase stiffness they may remain secure on the shoulders during normal movements of a wearer, and they may do so without experiencing excessive distortion of shape. However, it may be desirable to maintain a degree of elasticity in either or both of a bottom strap 16 and intermediate segments 20, 24 such that normal movements may be performed without a wearer being subjected to a significant resisting force. In some embodiments, a strap may be constructed from a single piece of material, and adjustment of the physical characteristics of a portion of the material piece made after the material is cut to a desired shape and/or size. Adjustment of a strap in this manner may be more efficient, provide a cost savings, or produce a strap that is stronger as compared to a strap produced using other methods, such as, for example, production of a strap from different pieces or different materials. In some embodiments, the physical properties of a strap or a portion of a strap useful for a posture reminder apparatus may be selected or adjusted by using a material with a desired set of properties, by forming a strap with a certain cross section, selecting a degree or orientation of stitching, through lamination of on one or both sides of a strap or strap portion, or with any combinations of the aforementioned techniques.

A connector 26, 28 may separate a shoulder loop portion 18, 22 of a strap 12, 14 from an associated intermediate segment 20, 24 of a given strap 12, 14. In the embodiment shown in FIG. 1, connectors 26, 28 may be buckles. The size of a given shoulder loop portion 18, 22 of a strap 12, 14 may be changed by adjusting the fitting of a strap end through an appropriate buckle 26, 28 and locking or engaging the buckle mechanism in place. A buckle may be secured at one position on a strap using a chape, and an end of the strap or other position on the strap secured in place using an adjustable or nonadjustable catch. In some embodiments, a connector element 26, 28 may include a hook, loop, male or female type connector element and an end of a strap may include a complementary element. Therefore, the connector elements 26, 28 may function as a part of a clasp. In some embodiments, connectors 26, 28 may be slideable and may or may not include a chape. Connector elements 26, 28 may, for example, be slide release buckles or strap adjuster buckles. A connector 26, 28 may, in some embodiments, include a body region and/or a slotted region. For example, a connector 26, 28 may be configured such that an end of a strap may be pulled through a first slot of the slotted region of the connector and then pulled through a second slot of the slotted region of the connector. An individual may adjust slack in the strap and then pull the strap so that a region of the strap becomes pressed against a bar which may be located between the two slots of the connector. The body region of a connector may, for example, include a hook, loop, male or female type fitting configured for connection to another part of a strap, strap end, or complementary fitting.

Figure 4:
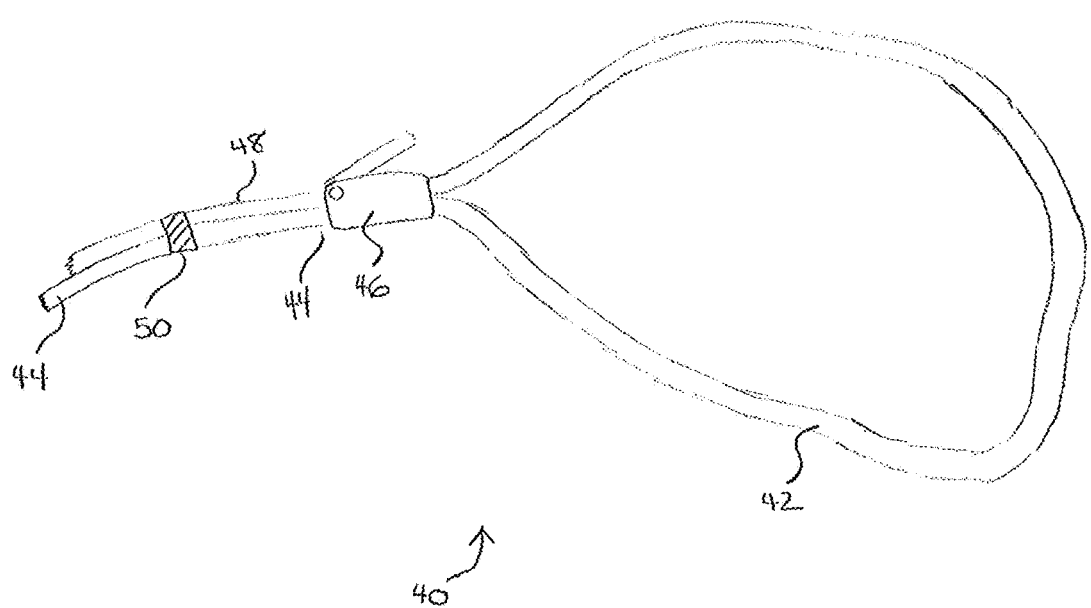
FIG. 4 shows an embodiment of a strap.

In some embodiments, a strap may be designed such that a loop is only formed if an end of the strap is inserted into a connector 26, 28. Alternatively, a loop may be formed by looping a strap and sewing or otherwise connecting a strap end to another portion of the strap. A sliding buckle or clamp may, in some embodiments, be slideable over the overlapping portion of the joined straps and locked in place as appropriate to adjust the size of a given shoulder loop portion 18, 22. Therefore, a strap may be permanently or semi-permanently fixed in a loop and yet a shoulder loop portion 18, 22 may be adjustable in size. FIG. 4 shows an embodiment of a strap 40 (which may be a right or left strap) including a shoulder loop portion 42 and part of an intermediate segment 44. FIG. 4 further shows a connector 46 that is slideable over a portion 48 of overlapping strap regions where the overlapping strap regions are connected at one or more places such as connected region 50. Connected region 50 may be a sewn region and a loop may be permanently formed once the region 50 is sewn, and the size of shoulder loop portion 42 may be adjusted by sliding and then locking connector 46 in place. However, region 50 may also be another element such as a clip or other suitable element configured to join two regions of a strap, and the region 50 may join the strap regions in a fixed or reversible manner. In addition, while a strap 40 may be made from a single piece of strap material, it may also be made from separate pieces of material. For example, two different pieces of material may be sewn together at a region 50 and also sewn at another region to complete shoulder loop portion 42 (such as, for example, shown in FIG. 5 below).

Figure 5:
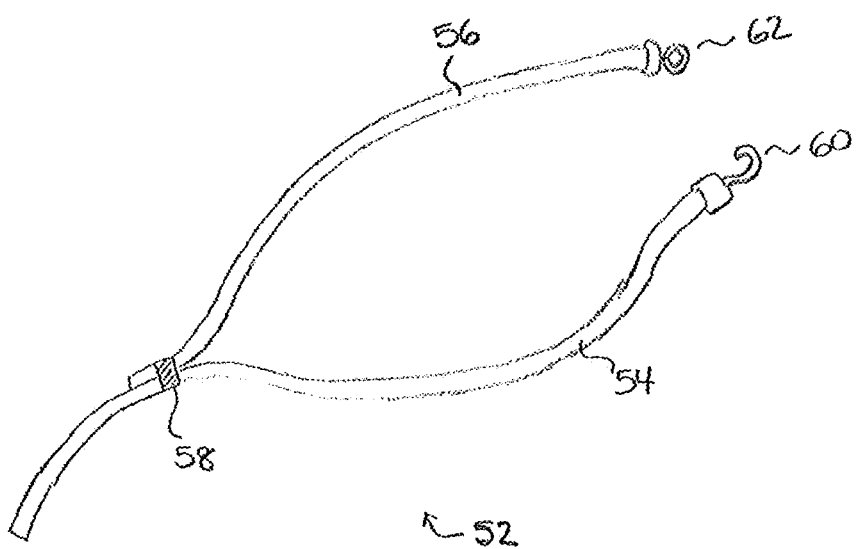
FIG. 5 shows an alternative embodiment of a strap.

In some embodiments, a connector may be formed by sewing or otherwise connecting (for example using a suitable element, such as a clip) two strap portions together. At the ends opposite the connected strap portions, clasp elements or adjustable buckles such as slide release buckles or strap adjuster buckles may be positioned. For example, FIG. 5 shows an exemplary embodiment of a strap 52 including two strap portions 54, 56 sewn together at a region 58. At the end of strap portion 54 a hook 60 may be placed, and at the end of strap portion 56 a loop 62 may be placed. In the embodiment of FIG. 5, the length of the two straps portions 54 and 56 may be configured such that hook 60 and loop 62 may be located at any convenient place along the strap 52. For example, strap portions 54, 56 may be sized such that the strap 52 may be easily hooked or adjusted from the front of a posture reminding apparatus when the apparatus is worn, which may be convenient for some wearers. In addition, in some embodiments, at the clasping end of either or both of strap portions 54, 56 an adjustable connector may be found. For example, a connector may be a forward facing adjustable connector located, for example, where the clasp ends 60, 62 are shown in FIG. 5, and that connector may include a body region and a slotted region. As discussed previously, an individual may adjust slack in a strap portion 54, 56 and then pull the strap portion so that a region of the strap portion becomes pressed against a bar which may be located between the two slots of the connector. The body region of a connector may, for example, include a hook, loop, male or female type fitting configured for connection to a complementary fitting (on the opposite strap portion). Therefore, reminder apparatuses described herein may be adjustable in various ways, such as by adjusting a connector 26, 28 (located where shoulder loop portions 18, 22 are connected to intermediate segments 20, 24) or by adjusting a different connector located at the front of a reminder apparatus. In some embodiments, shoulder loops of a reminder apparatus may be adjustable by a wearer with the apparatus worn, and the loops may be adjusted without the user reaching behind their back.

As shown in FIG. 1, connectors 26, 28 may divide a shoulder loop portion 18, 22 of a posture reminder apparatus 10 from the intermediate segments 20, 24. In some embodiments, a particular shoulder loop portion 18 or 22 and a particular intermediate segment 20 or 24 of the straps 12, 14 may be conveniently made from the same materials or same piece of one material. In addition, in some embodiments, both a right strap 12 and a left strap 14 may be made from a continuous piece of material. For example, a piece of material may be thread through connector 30 and one side of the material used for right strap 12 and the other side used for left strap 14. In other embodiments, each of right strap 12, left strap 14, and bottom strap 16 may be made from one continuous piece of material. For example, the bottom strap 16 may include a middle portion of the continuous piece of material that has been looped through fastener 32 and doubled back through connector 30, and opposite ends of the piece of material used for right strap 12 and left strap 14. In some embodiments, making a posture reminder apparatus from a continuous piece of material may include threading an end of the continuous piece of material through a slot or other portion of a connector 30, a fastener 32, and then back through the connector 30 a second time.

Figure 6:
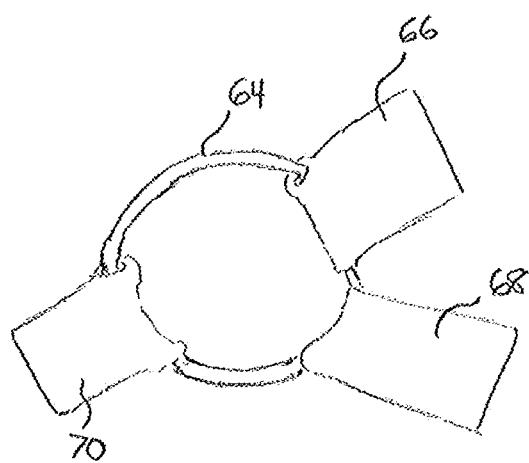
FIG. 6 shows an embodiment of a connector.

In some embodiments, connectors 26, 28 may be ring connectors (or may be configured with one or more slots of a convenient shape), and two ends of one or more pieces of a material making up a shoulder loop portion of a strap sewn or suitably connected to an end of the ring connector. The other end of a ring connector may be connected to a strap of an intermediate segment 20, 24. Use of a ring connector (or connector with one or more slots) may be a particularly convenient way to join shoulder loop portions 18, 22 and intermediate strap segments 20, 24 made from different materials. For example, in some embodiments, it may be desirable for an intermediate segment portion of a strap 20, 24 to possess a greater elasticity than a shoulder loop portion 18, 22 of a strap, and one convenient way to accomplish this may be to use strap portions that are made from different materials. FIG. 6 shows a connector ring 64 with both a first end 66 and a second end 68 of a shoulder loop portion connected to the connector ring 64. An end of an intermediate segment 70 is further shown in FIG. 6. In some embodiments, intermediate segment 70 may be neoprene and shoulder loop portions of a strap, such as ends 66 and 68, may be a fabric. In addition to providing materials that may be independently optimized for elasticity and/or resiliency, use of different materials for each of a shoulder loop portion of a strap and an intermediate segment of a strap may make provide an apparatus that is both comfortable to wear and enables a wearer to readily engage in normal motion, but still be able to provide a force to the shoulders if an individual slouches forward.

In some embodiments, shoulder loop portions 18, 22 and intermediate strap segments 20, 24 may be sized or processed such that the physical properties of the various straps are the same or different. The physical properties of either a shoulder loop portion 18, 22 or an intermediate segment portion 20, 24 of a strap may, for example, be selected or adjusted by using a material with a desired set of properties, selecting a certain cross section, selecting a degree or orientation of stitching, using lamination on one or both sides of a strap portion, or with any combination of the aforementioned techniques.

Intermediate strap segment 20, 24 may comprise material extending from connectors 26, 28 to the additional connector 30. Connector 30 may be fixedly or adjustably attached to intermediate strap segments 20, 24. For example, connector 30 may be a slideable element such as a slideable buckle that is adjustable with respect to the intermediate segments 20, 24. Therefore, it should be understood that the relative length of intermediate segments 20, 24 and bottom strap 16 may be adjusted. Adjustment of the connector 30 may change the relative length of the strap 16 and straps 20, 24 and thereby may also serve to adjust the orientation and angle of intermediate strap segments 20, 24. Generally, the position of connector 30 may be at a vertical position below the shoulder blades and above the belt line of a wearer. In some embodiments, an apparatus 10 may be configured such that a connector element 30 may be positioned between the beltline of the wearer and a vertical position that is about midway between the beltline and the wearer's shoulder blades. In some embodiments, an apparatus 10 may be configured such that a connector element 30 may be positioned between the beltline of the wearer and a vertical position that is no higher than about midway between the beltline and the wearer's shoulder blades. Also, as most clearly shown in FIG. 3, the connector 30 may be positioned along the axis of the spine of a wearer.

If an individual wearing a posture reminder apparatus 10 slouches forward, the apparatus 10 may be configured such that intermediate strap segments 20, 24 pull on the shoulder loop portions 18, 22 of the apparatus and the wearer may experience a force reminding the individual to adopt a correct posture. The orientation of forces on the shoulders may generally be related to the orientation and angle of the intermediate strap segments 20, 24. For example, a wearer of posture reminder apparatus 10 may generally experience a reminding force if they slouch forward that not only urges the shoulders backwards, but also directs the shoulders together and slightly downwards. Positioning a connector 30 closer to the beltline of an individual may configure an apparatus 10 to provide a reminding force that has a force with a vector component that is more vertical than if the connector were, for example, located between the shoulder blades. Such a force on the shoulders may naturally tend to direct the spine of an individual to a desired position and do so more effectively than techniques that simply press the shoulders together.

Bottom strap 16 may extend from connector 30 to a fastener 32. In some embodiments, bottom strap 16 may be made by looping a strap that is contiguous with both intermediate strap segments 20, 24. Alternatively, bottom strap 16 may be made from a strap that is continuous with one of right intermediate strap segment 18 or left intermediate strap segment 22, and the other intermediate strap segment stitched or bonded to bottom strap 16. Alternatively, bottom strap 16 may be a strap that is not continuous with either of the intermediate strap segments 20, 24. For example, connector 30 may be a ring, loop (or connector with one or more slots), and bottom strap 16 as well as the intermediate strap segments 20, 24 may be connected to the ring, loop or a slot. In some embodiments, the various straps 12, 14, and 16 of a posture reminder apparatus 10 may include a portion of material that is sewn to the connector 30.

At one end of bottom strap 16 and opposite connector 30, a fastener 32 may be attached. Fastener 32 may, for example, be a clip designed to secure apparatus 10 to an individual's trousers, skirt, belt, undergarment or other article of clothing. More generally, fastener 32 may be a clip, hook, string, latch, button, button loop, pin and cap, jaws, or other device suitable to removably secure bottom strap 16 to an article of clothing. It is also possible to connect intermediate strap segments 20, 24 directly to an element configured both to connect the straps and to fasten the intermediate strap segments 20, 24 to the beltline or trousers of an individual. However, in a preferred embodiment, bottom strap segment 16 is included in a posture reminder apparatus; the bottom strap segment 16, for example, provides an enhanced degree of adjustability to the apparatus, and thereby may facilitate configuration of the device for individuals of different heights and general body shapes.

Figure 7:
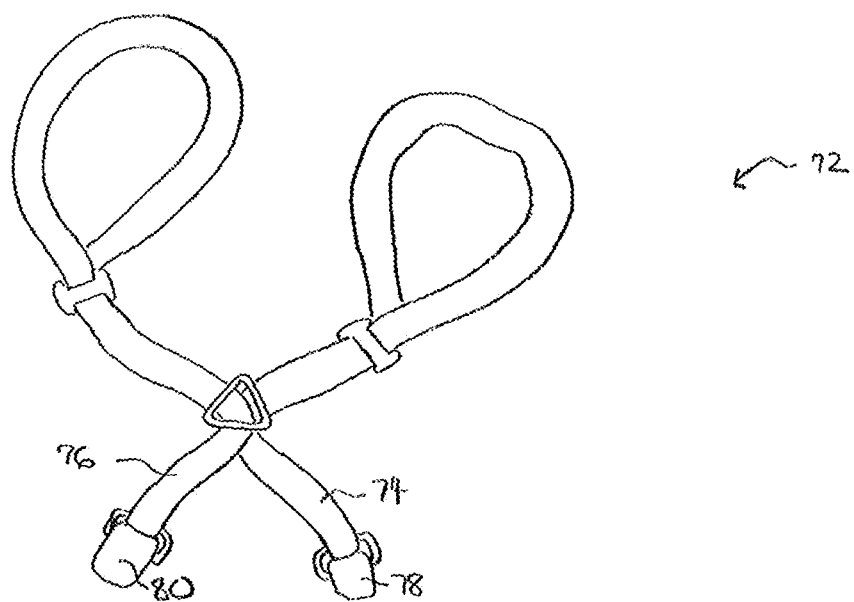
FIG. 7 shows another embodiment of an apparatus for reminding a wearer to maintain proper posture.

In some embodiments, a single bottom strap 16 may connect a posture reminding apparatus and a belt or other article of clothing. However, in other embodiments, a posture reminding apparatus may include a first and second bottom strap, and each of the first and second bottom straps may be configured for extension between a connector and a position near the waistline of a wearer. FIG. 7 shows an embodiment of a posture reminding apparatus 72 including a first bottom strap 74 and a second bottom strap 76. The bottom straps 74, 76 may each be connected to one of a pair of clips 78, 80.

Figure 8:
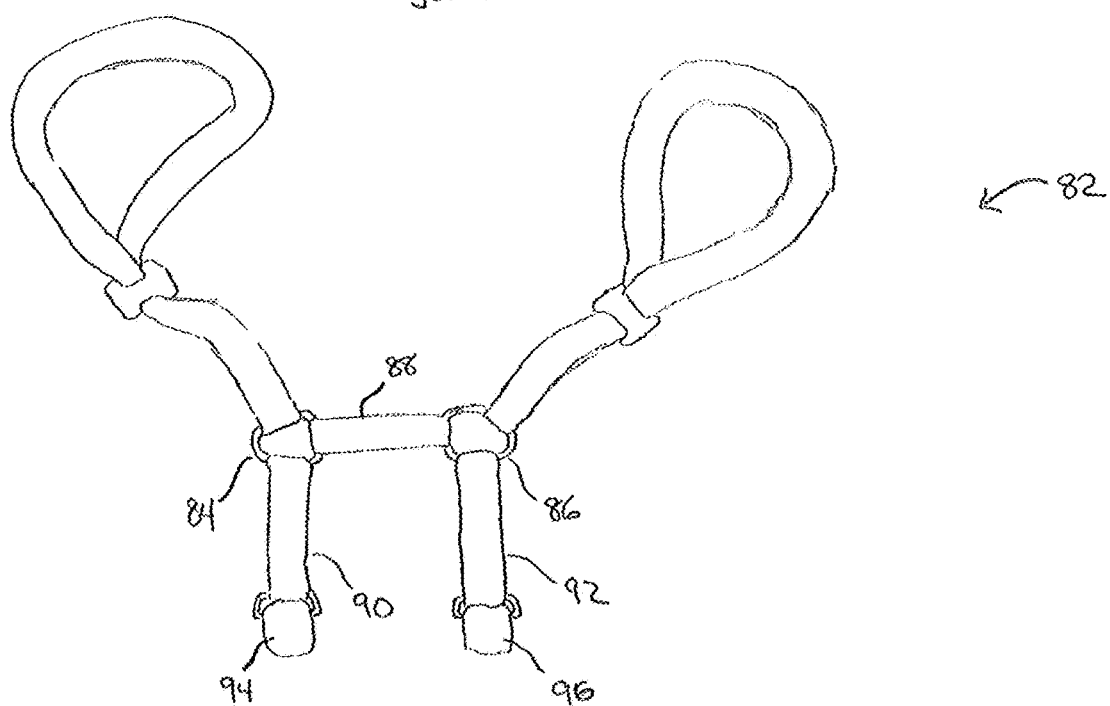
FIG. 8 shows still another embodiment of an apparatus for reminding a wearer to maintain proper posture.
Figure 9:
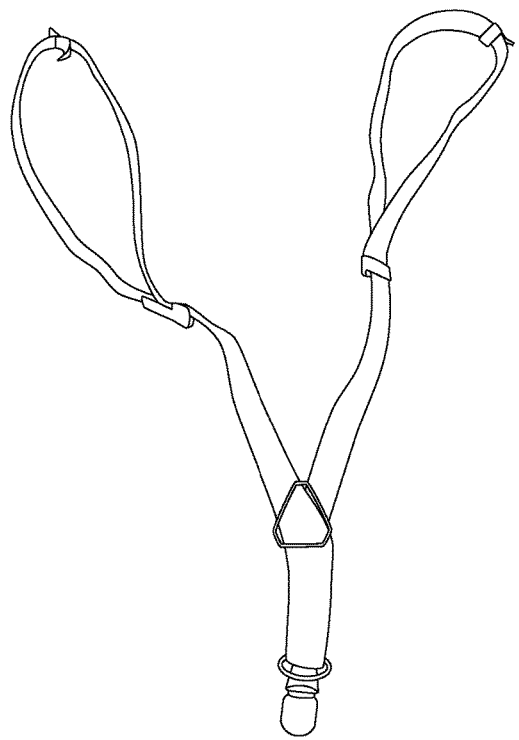
FIG. 9 shows still another embodiment of an apparatus for reminding a wearer to maintain proper posture.
Figure 10:
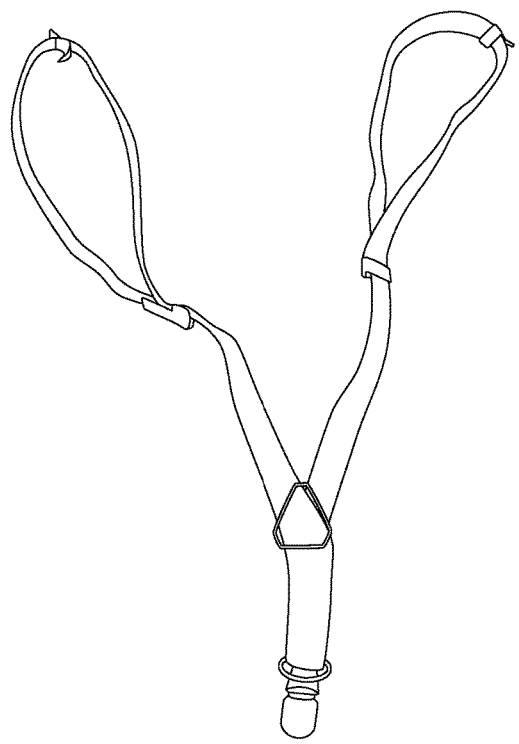
FIG. 10 shows still another embodiment of an apparatus for reminding a wearer to maintain proper posture.
Figure 11:
FIG. 11 shows an embodiment of an apparatus for reminding a wearer to maintain proper posture worn by an individual as viewed from the front.
Figure 12:
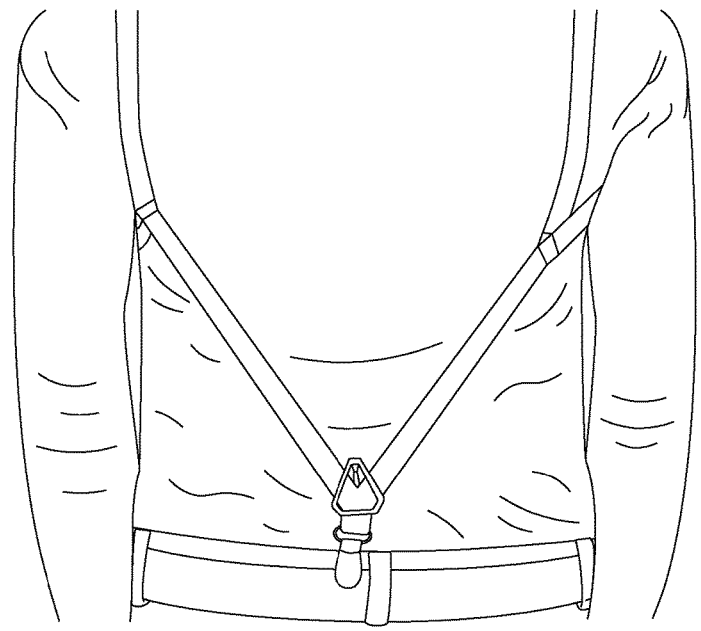
FIG. 12 shows an embodiment of an apparatus for reminding a wearer to maintain proper posture worn by an individual as viewed from the back.
Figure 13:
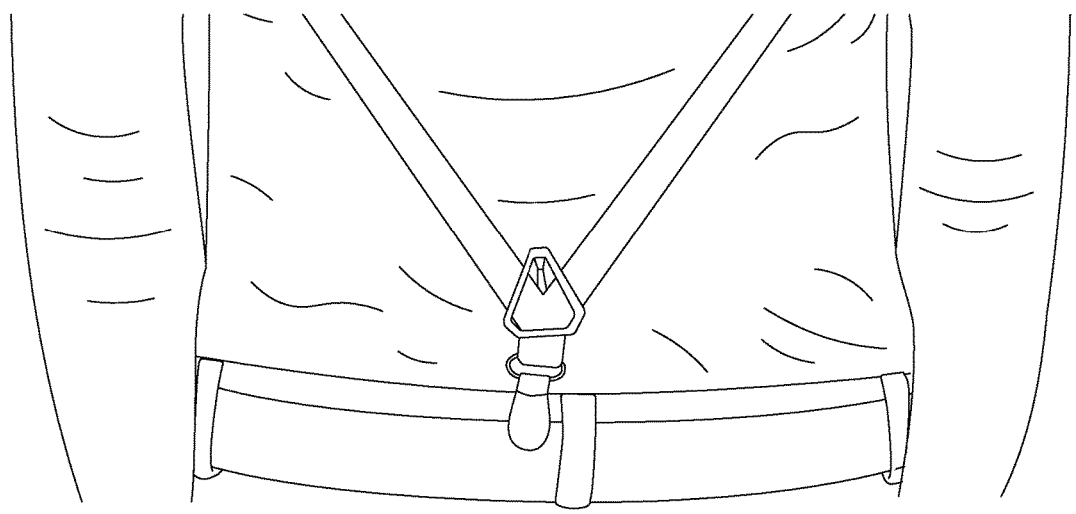
FIG. 13 shows an embodiment of an apparatus for reminding a wearer to maintain proper posture worn by an individual as viewed from the back.
Figure 14:
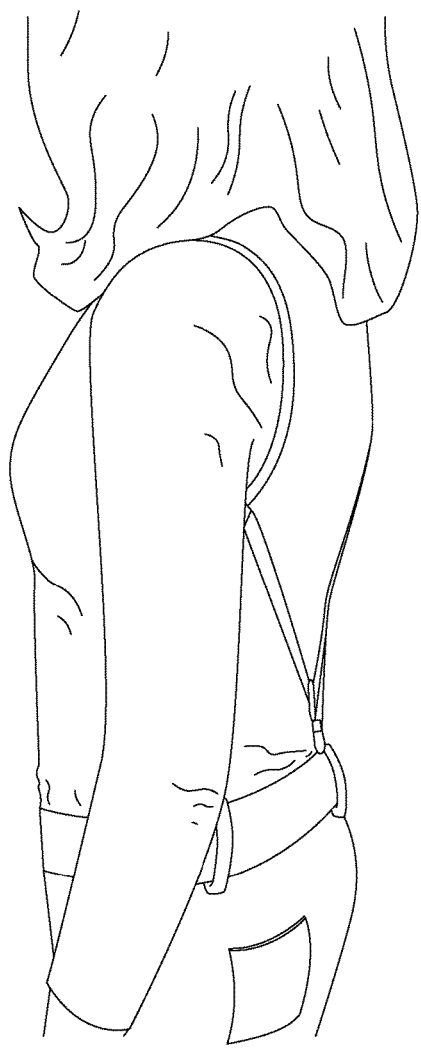
FIG. 14 shows an embodiment of an apparatus for reminding a wearer to maintain proper posture worn by an individual as viewed from the side.
Figure 15:
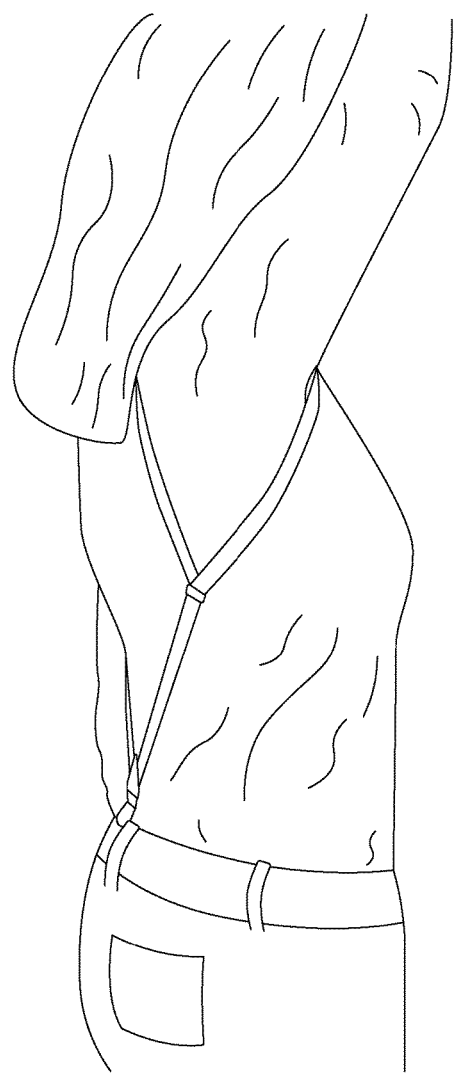
FIG. 15 shows an embodiment of apparatus for reminding a wearer to maintain proper posture worn by an individual as viewed from the side with the wearer raising her arm.

Referring to FIG. 8, another embodiment of a posture reminding apparatus 82 is shown in which right and left straps are connected to two different connectors 84 and 86. A center strap 88 may extend between the connectors 84 and 86. Center strap 88 may be of various lengths and/or may, in some embodiments, be adjustable such as to accommodate wearers of different sizes. A pair of bottom straps 90, 92 may each be connected to fastener clips 94, 96 and may facilitate reversible attachment of the posture reminder apparatus 82 to the belt or trousers of a wearer.

While many examples in this description refer to apparatuses, it is understood that those apparatuses are described in an exemplary manner only and that other apparatuses may be used. For example, any feature described for one embodiment may be used in any other embodiment. Additionally, other ingredients may be used, depending on the particular needs. Although the foregoing specific details describe certain embodiments, persons of ordinary skill in the art will recognize that various changes may be made in the details of these embodiments without departing from the spirit and scope of this invention as defined in the appended claims and other claims to be drawn to this invention, considering the doctrine of equivalents. Therefore, it should be understood that this invention is not limited to the specific details shown and described herein.

I claim:

1. An apparatus for encouraging a wearer to maintain proper posture comprising:

a first connector adapted to be positioned behind a back of the wearer and at a vertical position between shoulder blades and a waistline of said wearer when said apparatus is worn, and configured for joining a right strap and a first bottom strap;

a second connector adapted to be positioned behind the back of the wearer and at a vertical position between the shoulder blades and the waistline of said wearer when said apparatus is worn, and configured for joining a left strap and a second bottom strap;

wherein the right strap includes a closed loop adapted to be secured around a right shoulder of the wearer when said apparatus is worn and an intermediate segment;

wherein the right strap intermediate segment extends from the right strap closed loop to said first connector;

wherein the left strap includes a closed loop adapted to be secured around a left shoulder of the wearer when said apparatus is worn and an intermediate segment;

wherein the left strap intermediate segment extends from the left strap closed loop to said second connector;

wherein the first bottom strap is connected to said first connector at a first end and connected to a first fastener at another end;

wherein the second bottom strap is connected to said second connector at a first end and connected to a second fastener at another end; and a center strap extending between said first connector and said second connector;

wherein each of said first fastener and said second fastener are configured for attachment to an article of clothing near a beltline of said wearer when said apparatus is worn;

wherein the apparatus is configured such that if the wearer slouches forward a force sufficient to remind the user to adopt proper posture is applied by said left and said right straps to the shoulders of said wearer when said apparatus is worn.

2. The apparatus of claim 1 wherein the vertical position of both said first connector and said second connector is adapted to be no higher than about midway between the beltline and shoulder blades of the wearer of said apparatus when said apparatus is worn.

3. The apparatus of claim 2 wherein said force directs the shoulders together and downwards when said apparatus is worn.

4. The apparatus of claim 1 wherein at least one of said closed loops is adjustable in size.

5. An apparatus for encouraging a wearer to maintain proper posture comprising:

a first closed shoulder loop strap;

a first connector;

a first intermediate strap segment connected between said first closed shoulder loop strap and said first connector;

a second closed shoulder loop strap spaced apart from said first closed shoulder loop strap;

a second connector;

a second intermediate strap segment connected between said second closed shoulder loop strap and said second connector;

a center strap connected between said first connector and said second connector;

a first bottom strap depending from said first connector and having an end comprising a first fastener; and a second bottom strap depending from said second connector and having an end comprising a second fastener.

* * * * *